United States Patent
Xu et al.

(10) Patent No.: US 12,357,395 B2
(45) Date of Patent: Jul. 15, 2025

(54) METHOD AND SYSTEM FOR ESTIMATING POSITIONAL DATA IN IMAGES

(71) Applicant: Verb Surgical Inc., Santa Clara, CA (US)

(72) Inventors: Yiming Xu, Sunnyvale, CA (US); Juri Platonov, Munich (DE); Bernhard Adolf Fuerst, Mountain View, CA (US)

(73) Assignee: Verb Surgical Inc., Santa Clara, CA (US)

( * ) Notice: Subject to any disclaimer, the term of this patent is extended or adjusted under 35 U.S.C. 154(b) by 94 days.

(21) Appl. No.: 18/062,512

(22) Filed: Dec. 6, 2022

(65) Prior Publication Data

US 2024/0180624 A1    Jun. 6, 2024

(51) Int. Cl.
*A61B 34/20* (2016.01)
*G06T 7/00* (2017.01)

(52) U.S. Cl.
CPC ............ *A61B 34/20* (2016.02); *G06T 7/0012* (2013.01); *A61B 2034/2065* (2016.02); *G06T 2207/10028* (2013.01); *G06T 2207/10068* (2013.01)

(58) Field of Classification Search
CPC ...... A61B 2034/105; A61B 2034/2065; A61B 34/20; G06T 2207/10028; G06T 2207/10068; G06T 7/0012
See application file for complete search history.

(56) References Cited

U.S. PATENT DOCUMENTS

| | | | |
|---|---|---|---|
| 9,492,240 | B2 | 11/2016 | Itkowitz et al. |
| 2003/0181920 | A1 | 9/2003 | Hawkins et al. |
| 2005/0159759 | A1 | 7/2005 | Harbaugh et al. |
| 2019/0365209 | A1 | 12/2019 | Ye et al. |
| 2020/0045293 | A1 | 2/2020 | Honda |
| 2020/0093544 | A1* | 3/2020 | Azizian ................. G06T 7/0012 |
| 2022/0087768 | A1 | 3/2022 | Mai et al. |

FOREIGN PATENT DOCUMENTS

KR    20210136975 A    11/2021

OTHER PUBLICATIONS

International Search Report and Written Opinion of the International Searching Authority received for PCT Patent Application No. PCT/IB2023/062017, mailed on Mar. 7, 2024, 9 pages.

* cited by examiner

*Primary Examiner* — Mark D Remaly
(74) *Attorney, Agent, or Firm* — Aikin & Gallant, LLP

(57) ABSTRACT

A method performed by a surgical system. The method includes receiving a first image from an endoscope, the first image having a surgical instrument at a first location within a field of view of the endoscope. The method matches a three-dimensional (3D) model of the surgical instrument to the first image. The method receives a second image receives a second image from the endoscope, the second image having the surgical instrument at a second location within the field of view of the endoscope, and matches the 3D model of the surgical instrument to the second image. The method estimates a distance between the first and second locations based on both matchings and one or more parameters of the endoscope.

7 Claims, 9 Drawing Sheets

Fourth Stage 53

Fifth Stage 54

Sixth Stage 55

METHOD AND SYSTEM FOR ESTIMATING POSITIONAL DATA IN IMAGES

FIELD

Various aspects of the disclosure relate generally to surgical systems, and more specifically to a surgical system that estimates positional data (e.g., distances between locations) in images. Other aspects are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool drive having one or more motors may actuate one or more degrees of freedom of a surgical tool when the surgical tool is positioned at the surgical site in the patient.

SUMMARY

A laparoscopic surgery may involve the insertion of several surgical tools, such as an endoscope, a blade, and a grasper into (e.g., an abdomen of) a patient. To perform the surgery, a surgeon may view (e.g., in real-time) a surgical site and the surgical tools within the patient through video (images) captured by the endoscope that is displayed on a display, and may perform surgical tasks upon (or at) the surgical site by manipulating the surgical tools. For example, to perform an incision upon the surgical site, the surgeon may manipulate a blade while viewing the incision on the display.

During (and/or after) the surgery, a surgeon may need to determine positional data related to the surgical site. Returning to the previous example, before making the incision, the surgeon may need to determine a distance (or length) along the surgical site to cut with the blade. This distance may be estimated in cases in which the endoscope is a stereoscopic camera that is capturing stereoscopic video. For example, a surgical system may estimate a distance between two points captured by two separate cameras (based on the relative positions of the cameras with respect to one another). In cases, however, when the endoscope is a monocular camera, the distance may not be estimated due to there being only one camera. As a result, surgeons have relied on using physical rulers to take measurements, which may be cumbersome and inaccurate. Thus, there is a need for a surgical system that is configured to (e.g., intraoperatively) estimate positional data, such as distances along a surgical site using one or more images captured by a (e.g., monocular) camera, such as an endoscope.

The present disclosure provides a surgical system that intraoperatively (and/or post operatively) estimates positional data using images. In particular, the system receives a first image from an endoscope, the first image having a surgical instrument at a first location within a field of view of the endoscope. For instance, the first image may show the surgical instrument as the surgeon is touching a location of an object (e.g., tissue). The system matches a three-dimensional (3D) model of the surgical instrument to the first image. For example, the system may adjust the model (e.g., in a 3D space) in order to match the position and/or orientation of the surgical instrument. The system receives a second image from the endoscope, the second image having the surgical instrument at a second location within the field of view of the endoscope. In this case, the surgeon may have moved the surgical instrument and touched a different location of the object, wanting to measure the distance between the two points. The system matches the 3D model of the surgical instrument to the second image. Again, the system may manipulate the model to a new position and/or orientation to match the instrument. The system estimates the distance between the two locations based on both matchings and one or more parameters of the endoscope (e.g., a focal length of the lens of the endoscope). Thus, the system may estimate the distance based on a relative transformation between the two 3D models matched with the surgical instrument at the two locations, which allows the system to provide the distance to the surgeon, regardless of whether the endoscope is a monocular camera (or a stereoscopic camera).

In one aspect, the one or more parameters of the endoscope include at least one of a focal length of a lens of the endoscope, a principal point associated with the lens, and a distortion of the lens. In another aspect, the system estimates a first six dimensional (6D) pose of the surgical instrument at the first location based on the one or more parameters of the endoscope and the matching 3D model of the surgical instrument in the first image, estimates a second 6D pose of the surgical instrument at the second location based on the one or more parameters of the endoscope and the matching 3D model of the surgical instrument in the second image, where the distance is estimated using the first and second 6D poses. In some aspects, the second image is received after the first image, where the system further determines that the endoscope has moved from a first position at which the first image was captured by the endoscope to a second, different position at which the second image was captured by the endoscope, where the second 6D pose is determined based on the movement of the endoscope.

In one aspect, the first and second locations are on a portion of an object that is within the first and second images, where the second image is of a different perspective of the object than the first image, where the system further determines a 3D reconstruction of the portion of the object based on the first and second images, where the estimated distance is of a path along the 3D reconstruction of the portion of the object between the first and second locations.

In one aspect, the surgical instrument is arranged to be manually manipulated by a user. In another aspect, the system displays 1) a first marker at the first location and a second marker at the second location and 2) the estimated distance overlaid on top of the second image.

The above summary does not include an exhaustive list of all aspects of the disclosure. It is contemplated that the disclosure includes all systems and methods that can be practiced from all suitable combinations of the various aspects summarized above, as well as those disclosed in the Detailed Description below and particularly pointed out in the claims. Such combinations may have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect of this disclosure are not necessarily to the same aspect, and they mean at least one. Also, in the interest of conciseness and reducing the total number of figures, a given figure may be used to illustrate the features of more than one aspect, and not all elements in the figure may be required for a given aspect.

DETAILED DESCRIPTION

Several aspects of the disclosure with reference to the appended drawings are now explained. Whenever the shapes, relative positions and other aspects of the parts described in a given aspect are not explicitly defined, the scope of the disclosure here is not limited only to the parts shown, which are meant merely for the purpose of illustration. Also, while numerous details are set forth, it is understood that some aspects may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
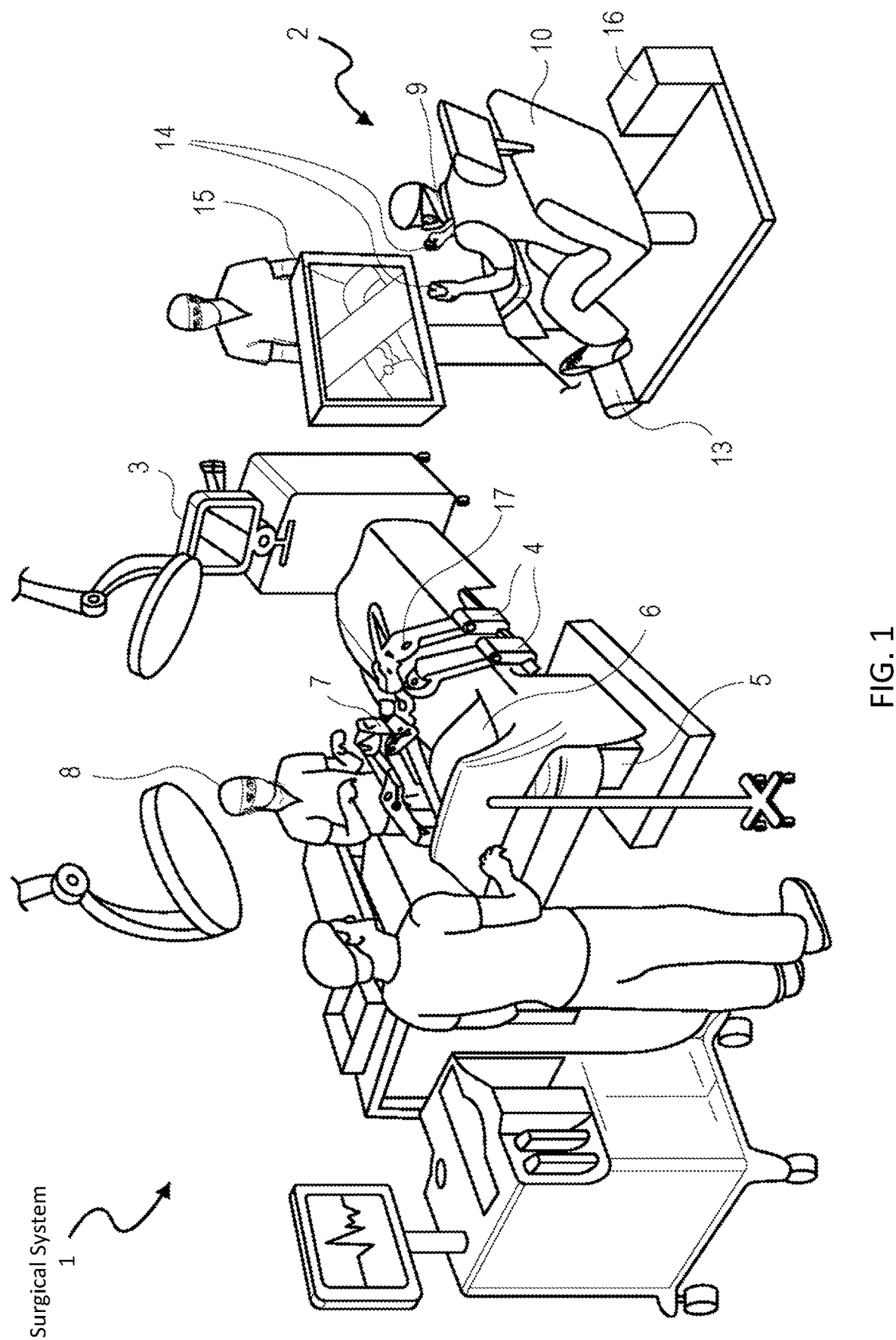
FIG. 1 shows a pictorial view of an example surgical system in an operating arena.

FIG. 1 shows a pictorial view of an example (e.g., laparoscopic) surgical system (which hereafter may be referred to as "system") 1 in an operating arena. The system 1 includes a user console 2, a control tower 3, and one or more surgical robotic arms 4 at a surgical robotic table (surgical table or surgical platform) 5. In one aspect, the arms 4 may be mounted to a table or bed on which the patient rests as shown in the example of FIG. 1. In one aspect, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools (instruments) 7 used to perform surgery (surgical procedure). A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, perform a surgical task, and/or manipulate an internal anatomy of the patient 6. In an aspect, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. For example, when manually controlled an operator may (e.g., physically) hold a portion of the tool (e.g., a handle), and may manually control the tool by moving the handle and/or pressing one or more input controls (e.g., buttons) on the (e.g., handle of the) tool. In another aspect, when controlled robotically, the surgical system may manipulate the surgical tool based user input (e.g., received via the user console 2, as described herein).

Generally, a remote operator 9, such as a surgeon or other operator, may use the user console 2 to remotely manipulate the arms 4 and/or the attached surgical tools 7, e.g., during a teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and at least one display 15. The display is configured to display, for example, a view of the surgical site inside the patient 6. The display may be configured to display image data (e.g., still images and/or video). In one aspect, the display may be any type of display, such as a liquid crystal display (LCD), a light-emitting diode (LED) display, an organic LED (OLED) display, a head-mounted display (HMD), etc. In some aspects, the display may be a 3D immersive display that is for displaying 3D (surgical) presentations. For instance, during a surgical procedure one or more endoscopes (e.g., endoscopic cameras) may be capturing image data of a surgical site, which the display presents to the user in 3D. In one aspect, the 3D display may be an autostereoscopic display that provides 3D perception to the user without the need for special glasses. As another example, the 3D display may be a stereoscopic display that provides 3D perception with the use of glasses (e.g., via active shutter or polarized).

In another aspect, the display 15 may be configured to display at last one graphical user interface (GUI) that may provide informative and/or interactive content, to thereby assist a user in performing a surgical procedure with one or more instruments in the surgical system 1. For example, some of the content displayed may include image data captured by one or more endoscopic cameras, as described herein. In another aspect, the GUI may include selectable UI items, which when manipulated by the user may cause the system to perform one or more operations. For instance, the GUI may include a UI item as interactive content to switch control between robotic arms. In one aspect, to interact with the GUI, the system may include input devices, such as a keyboard, a mouse, etc. In another aspect, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some aspects, the display may be a touch-sensitive display screen. In this case, the user may perform a selection by navigating and selecting through touching the display. In some aspects, any method may be used to navigate and/or select a UI item.

As shown, the remote operator 9 is sitting in the seat 10 and viewing the user display 15 while manipulating a foot-operated control 13 and a handheld UID 14 in order to remotely control one or more of the arms 4 and the surgical tools 7 (that are mounted on the distal ends of the arms 4.)

In some variations, the bedside operator 8 may also operate the system 1 in an "over the bed" mode, in which the beside operator (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the system 1 are in a stowed configuration or withdrawn configuration (to facilitate access to the surgical site.) Once access is completed, initial positioning or preparation of the system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one aspect, the remote operator 9 holds and moves the UID 14 to provide an input command to drive (move) one or more robotic arm actuators 17 (or driving mechanism) in the system 1 for teleoperation. The UID 14 may be communicatively coupled to the rest of the system 1, e.g., via a console computer system 16 (or host). The UID 14 can generate spatial state signals corresponding to movement of the UID 14, e.g., position and orientation of the handheld housing of the UID, and the spatial state signals may be input signals to control motions of the robotic arm actuators 17. The system 1 may use control signals derived from the spatial state signals, to control proportional motion of the actuators 17. In one aspect, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the system 1. The system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable one of a variety of wireless data communication protocols, such as BLUETOOTH protocol. Any wired connections may be optionally built into the floor and/or walls or ceiling of the operating room. The system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
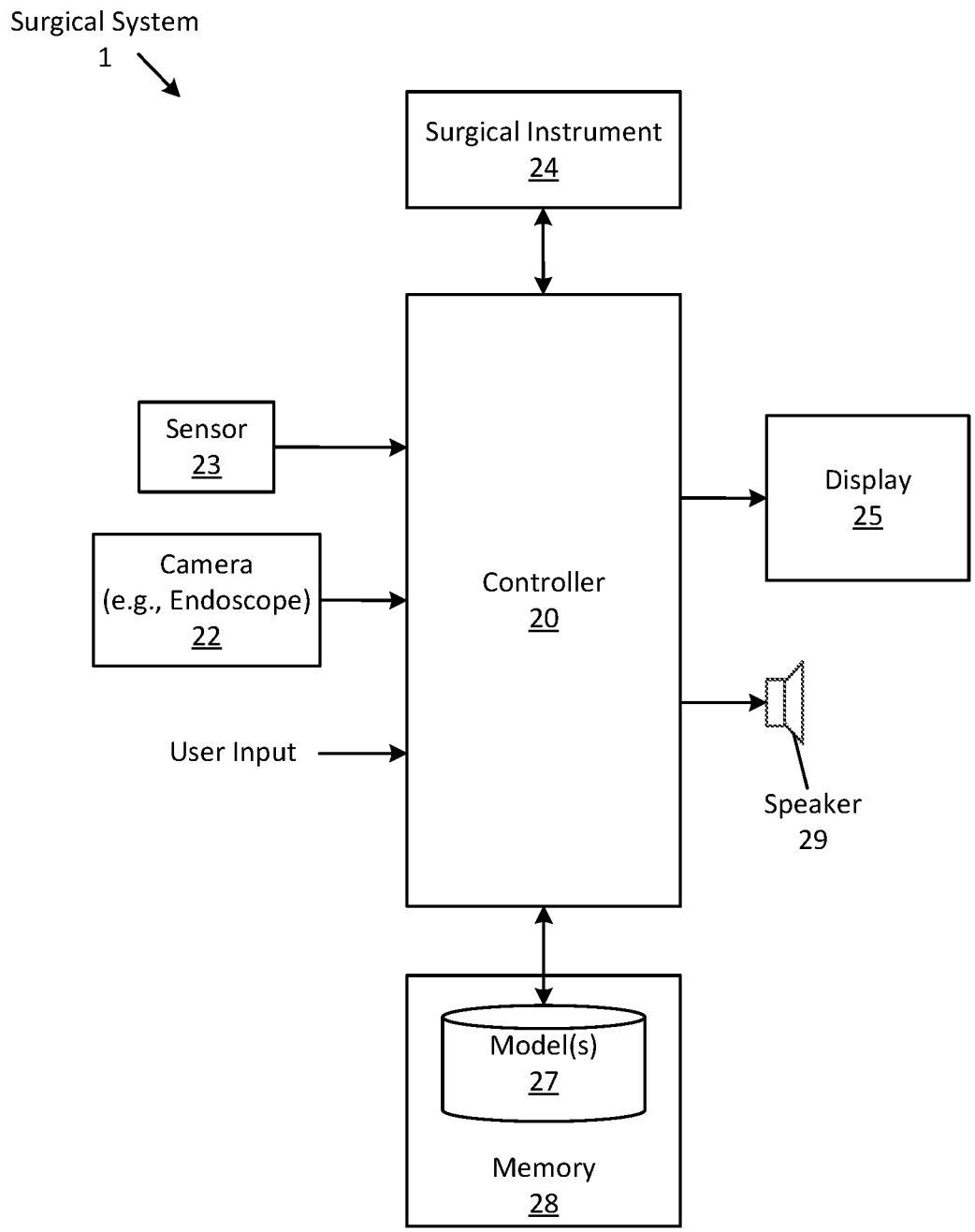
FIG. 2 is a block diagram of the surgical system that includes estimates positional data within images according to one aspect.

FIG. 2 is a block diagram of the surgical system 1 that includes estimates positional data within images according to one aspect. The system includes one or more (e.g., electronic) components (or elements), such as a controller 20, a camera (e.g., endoscope) 22, a sensor 23, a surgical instrument 24, a display 25, a speaker 29, and memory 28. In one aspect, the system may include more or less elements, such as having one or more surgical instruments and/or having one or more (e.g., different) sensors 23. In another aspect, the surgical system 1 may include other elements that are not shown, such as having one or more robotic arms to which the surgical instrument 24 may be coupled.

In some aspects, at least some of the elements may be a part of (or housed within a housing of) a single electronic device. For example, the controller 20 and the memory 28 may be a part of the control tower 3 of the surgical system 1. In another aspect, at least some of the elements may be separate (or a part of separate) electronic devices with respect to each other. For example, the sensor 23 may be a separate electronic device that may be positioned within an operating arena in which (or a part of which) the surgical system is located. In one aspect, the elements of the surgical system may be communicatively coupled with the controller 20 (and/or one another) in order to exchange digital data. For instance, the controller 20 may be configured to receive sensor data from the sensor 23 via a wired (and/or wireless) connection.

In the case of a wireless connection, the controller may be configured to wirelessly communicate, via a network, with one or more elements, such as the sensor 23 (e.g., to exchange data). In one aspect, devices may communicate via any (computer) network, such as a wide area network (WAN) (e.g., the Internet), a local area network (LAN), etc., through which the devices may exchange data between one another and/or may exchange data with one or more other electronic devices, such as a remote electronic server. In another aspect, the network may be a wireless network such as a wirelessly local area network (WLAN), a cellular network, etc., in order to exchange digital data. With respect to the cellular network, the controller (e.g., via a network interface) may be configured to establish a wireless (e.g., cellular) call, in which the cellular network may include one or more cell towers, which may be part of a communication network (e.g., a 4G Long Term Evolution (LTE) network) that supports data transmission (and/or voice calls) for electronic devices, such as mobile devices (e.g., smartphones). In another aspect, the devices may be configured to wirelessly exchange data via other networks, such as a Wireless Personal Area Network (WPAN) connection. For instance, the controller may be configured to establish a wireless communication link (connection) with an element (e.g., an electronic device that includes the sensor 23) via a wireless communication protocol (e.g., BLUETOOTH protocol or any other wireless communication protocol). During the established wireless connection, the electronic device may transmit data, such as sensor data as data packets (e.g., Internet Protocol (IP) packets) to the controller 20.

The camera 22 (e.g., a complementary metal-oxide-semiconductor (CMOS image sensor) is an electronic device that is configured to capture video (and/or image) data (e.g., as a series of still images). In one aspect, the camera may be an endoscope that is designed to capture video of a surgical site within a body of a patient during a surgical procedure. In one aspect, the camera may be a monocular camera that (e.g., has a single camera sensor that) captures one digital image (e.g., a still image) at a time (e.g., to produce an endoscopic video stream). In another aspect, the camera may be a stereoscopic (stereo) camera with two (or more) lenses, each with a separate camera sensor for capturing individual still images (e.g., for producing separate video streams) in order to create 3D video.

The surgical instrument (or tool) 24 may be any type of surgical instrument that is designed to be used during a surgical procedure, and includes an end effector for performing one or more surgical tasks. For example, the surgical instrument may be a grasper for grabbing and grasping objects, an ultrasonic instrument that uses ultrasonic vibration (e.g., at its tip) to rapidly generate heat for cutting and cauterizing tissue, a scalpel, etc. In one aspect, the camera and surgical instrument may be manipulated manually, robotically, or both during a surgical procedure, as described herein. For instance, the surgical instrument 24 may include a handle (coupled to its proximal end) that is configured to be held by an operator and allows the operator to manually control (e.g., the position, orientation, and configuration) of the (e.g., distal end of the) surgical instrument. Thus, the surgical instrument may be arranged to be manually manipulated by a user (e.g., surgeon).

The sensor 23 may be any type of electronic device that is configured to detect (or sense) the environment (e.g., an operating room) and produce sensor data based on the environment. For example, the sensor 23 may include at least one microphone that may be configured to convert acoustical energy caused by sound wave propagation into an input microphone signal (or audio signal). In another aspect, the sensor may be a proximity sensor (e.g., an optical sensor) that is configured to detect a presence of one or more objects within the environment. In another aspect, the sensor may be a temperature sensor that senses an ambient temperature (e.g., within a room in which the sensor is located) as sensor data.

In some aspects, the sensor may be a motion sensor (e.g., an inertial measurement unit (IMU)) that is designed to measure a position and/or orientation. For example, the IMU may be coupled to (or a part of) the camera 22, and may be configured to detect motion (e.g., changes in the camera's position and/or orientation) of the camera (e.g., due to an operator manipulating the camera in order to show a different perspective of a surgical site during a surgical procedure). In some aspects, the motion sensor may be a camera that captures images used by the controller 20 to perform motion tracking operations (e.g., based on changes in the captured images).

The memory (e.g., non-transitory machine-readable storage medium) 28 may be any type of electronic storage device. For example, the memory may include read-only memory, random-access memory, CD-ROMS, DVDs, magnetic tape, optical data storage devices, flash memory devices, and phase change memory. Although illustrated as being separate from the controller 20, the memory may be a part of (e.g., internal memory of) the controller 20. As shown, the memory 28 includes one or more 3D (e.g., computer-aided design (CAD)) models 27 of one or more surgical instruments 24 of the surgical system. In particular, each of the models may be a graphical mathematical coordinate-based representation (e.g., as one or more basis (or B-)splines, such as non-uniform rational basis splines (NURBSs)) of (at least a portion of) a surgical instrument. For example, when the instrument is a surgical grasper that includes grasping/clamping distal portion coupled to a shaft, the 3D model may be a representation of the grasping/clamping distal portion. In one aspect, each model may include one or more different orientations of a corresponding instrument within a 3D coordinate system (e.g., Cartesian coordinate system), with respect to a reference point. In some aspects, at least some of the models may be predefined (e.g., provided to the surgical system 1 via a communication link with an electronic device (e.g., a remote server) that generated (and/or stored) the models). For example, one or more of the models may be generated and provided by a manufacturer of a corresponding surgical instrument. In another aspect, one or more of the models may be periodically updated in (and/or added into) the memory 28 of the surgical system.

The controller 20 may be any type of electronic component that is configurable to perform one or more computational operations. For example, the controller may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). The controller 20 is configured to receive image data (e.g., as a video stream) captured by the camera 22 and is configured to perform positional data estimation, such as estimating a distance between two points within one or more images using one or more models 27 of one or more surgical instruments that are captured within the images. Such operations may allow operators of the surgical system 1 to perform intraoperative positional measurements using images captured by a monocular camera. More about how the controller estimates the positional data is described herein.

In one aspect, the controller may be configured to receive user input through one or more input (electronic) devices (not shown). For example, the controller 20 may be coupled to one or more (e.g., peripheral computer) input devices, such as a keyboard or a mouse through which user input may be received. In another aspect, user input may be received through a touch-sensitive display (e.g., display 25), which may display a graphical user interface (GUI) with one or more user interface (UI) items, where the device may produce one or more control signals (as the user input) based on an operator touching a portion of the touch-sensitive display that is presenting a UI item (of interest to the operator). In some aspects, the touch-sensitive display may be a part of an electronic device, such as a tablet computer, a laptop computer, or a smart phone.

FIGS. 3a-3b, 5, and 6 are flowchart of processes for aspects of estimating positional data. In one aspect, at least some of the operations of at least some of the processes may be performed intraoperatively (e.g., while a surgeon is performing a surgical (e.g., laparoscopic) procedure upon a patient). In another aspect, at least some of the operations may be performed postoperatively (e.g., based on video captured during a surgical procedure). More about how the operations may be performed postoperatively is described herein. In some aspects, at least some of the operations of at least some of the processes may be performed by the (e.g., controller 20 of the) surgical system 1, described herein.

Figure 3A:
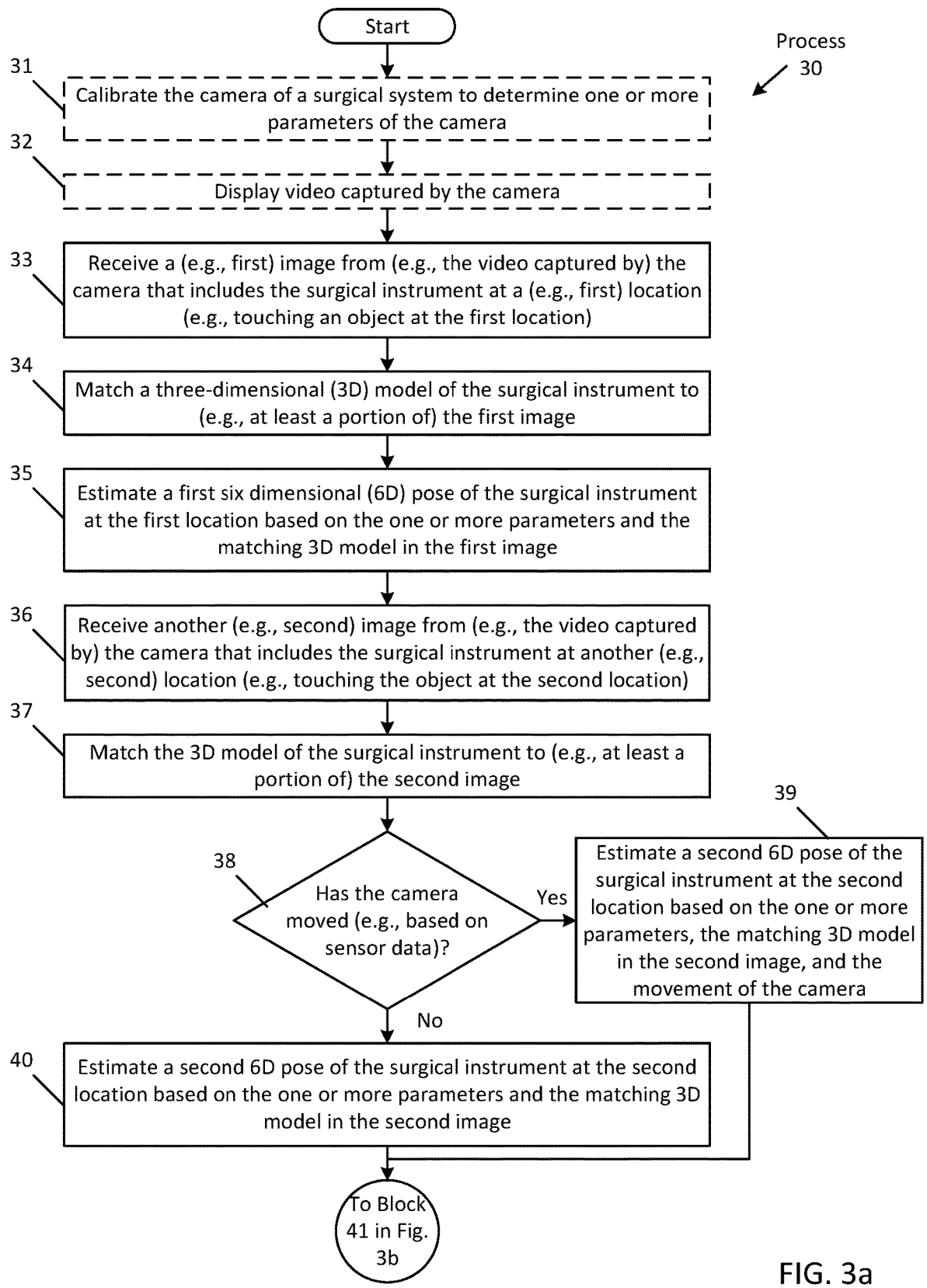
FIGS. 3a and 3b is a flowchart of a process for an aspect of estimating a distance between two locations.
Figure 3B:
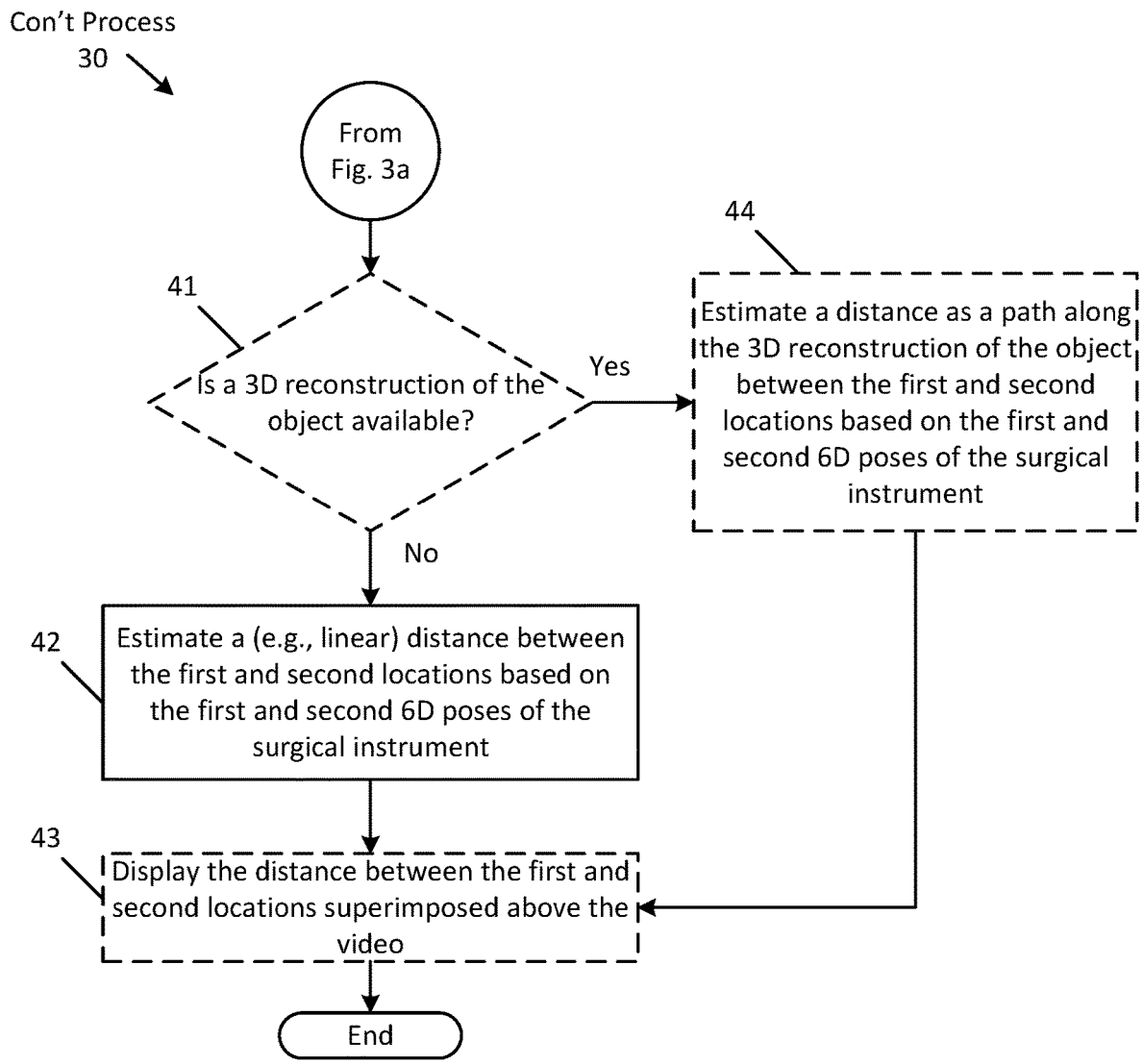

Turning now to FIGS. 3a and 3b, these figures show a flowchart of a process 30 for an aspect of estimating a distance between two locations. The process 30 begins by the controller 20 calibrating a camera 22 (e.g., a monocular endoscope) of the surgical system 1 to determine one or more (e.g., intrinsic) parameters of (e.g., components, such as a lens and/or image sensor of) the camera (at block 31). In one aspect, the parameters may be intrinsic parameters of the camera that are associated with this particular camera (e.g., being associated with physical attributes of the camera). In some aspects, these intrinsic parameters may include at least one of a focal length of (e.g., a lens of) the camera, a principal point (or optical center) of the (e.g., lens of the) camera, a skew of the camera, and a distortion of the lens of the camera. In some aspects, to calibrate the camera to determine the parameters, the controller may perform a calibration algorithm that uses one or more images captured by the camera and one or more characteristics (e.g., extrinsic) parameters, such as the position and/or orientation of the camera. In some aspects, the calibration algorithm may be based on the type of camera of the surgical system (e.g., whether the camera is a pinhole camera). In another aspect, the controller may perform any type of calibration (e.g., algorithm) to determine the one or more parameters.

In one aspect, the calibration may be performed by a manufacturer of the camera. In which case, the controller may perform the calibration may retrieving the one or more parameters. In another aspect, the calibration may be performed "in-field", meaning that the calibration may be performed by the surgical system prior to (or during) a surgical procedure. In some aspects, the calibration may be performed once, such during an initial power up of the camera when the camera is first connected to the surgical system 1. As another example, the calibration may be performed the first time the camera is coupled to the controller 20 and provided power. Once the calibration is complete, the controller may store (and use) the one or more parameters to estimate positional data, as described herein. In another aspect, the camera may be periodically (e.g., once a week) calibrated.

The controller 20 displays video captured by the camera on the display 25 (at block 32). In one aspect, the captured video may be displayed in real time. In particular, the camera may be capturing video of a surgical site during a surgical procedure, and the surgical system may be displaying the captured video for a surgeon to view during the procedure. The controller 20 receives an (e.g., first) image from (e.g., video captured by) the camera that includes a surgical instrument 24 at a (e.g., first) location within a field of view of the camera, e.g., touching an object at the first location (at block 33). In particular, the image includes a field of view of the camera that may include (at least a partial view of) a surgical site (e.g., within a cavity of a patient) that has one or more objects (e.g., tissue, fluid, etc.), and includes at least a portion of the surgical instrument, such as a distal portion with which a surgeon may perform one or more surgical tasks. As described herein, the distal portion may be a grasper. In one aspect, the surgical instrument may have one or more degrees of freedom within the surgical space, such has having six degrees of freedom (6DOF) that allows the instrument to be (e.g., manually) translated and/or rotated along at least one of three perpendicular axes.

In one aspect, the first image may be one of a series of images that are being captured (or have been captured) by the camera, and are being displayed on the display 25 (e.g., as described in block 32). In another aspect, the first image may be a first image captured by the camera when the camera is activated (e.g., when the camera is powered on). In some aspects, the first image may be received based on (e.g., responsive to) user input (received by the controller 20). In particular, the surgeon may move the surgical instrument to the first location such that (e.g., a portion of) the surgical instrument is at (or adjacent to) and/or touching the first location (e.g., from where the surgeon wishes to estimate positional data, such as a distance), and the controller may receive the first image responsive to receiving user input. For example, once moved to the location, input may be received through an input device (e.g., the surgeon may press a (e.g., physical) button of an electronic device (e.g., a mouse) that is coupled to the controller, which produces and transmits a control signal to the controller based on the input. Once input is received, the controller may retrieve (draw) the first image captured by the camera. In another aspect, responsive to the user input, the camera may capture the first image. In another aspect, user input may be received in other ways, such as through a voice command. In which case, when the surgeon wishes for the surgical system to capture the first image, the surgeon may utter a phrase of one or more words. In response, a microphone (e.g., as a sensor 23) may capture the phrase and perform a voice detection algorithm to detect the phrase contained therein. Upon detecting the phrase, the controller may receive (capture) the first image.

As described herein, the first image may be captured responsive to user input. In another aspect, the first image may be captured automatically (e.g., without user intervention). For example, the controller 20 may receive the first image based on an object recognition algorithm (that is being executed by the controller 20). In particular, the controller 20 may determine whether positional data is to be estimated based on a recognition of one or more objects (and/or the first location) within the first image. As described herein, the estimation of the positional data may be performed during a surgical procedure. In which case, the procedure may include one or more surgical tasks, which are known to the controller, such as an estimation of positional data. The controller may be configured to receive the first image (for position estimation) based on a determination that the object detected within the video stream captured by the camera is associated with the surgical task that includes estimating the positional data. In another aspect, the controller may be configured to receive the first image based on a determination that the surgical instrument has remained at the first location for a period of time. As another example, the controller may be configured to receive the first image based on a determination that the surgical instrument or more specifically a distal end of the surgical instrument is pressing against (in contact with or touching) an object within the field of view of the camera 22. In one aspect, the controller may determine whether the surgical instrument is in contact with the object based on sensor data obtained by the sensor 23. For instance, when the sensor is a pressure sensor that is coupled to the surgical instrument, it may produce sensor data indicating that the surgical instrument is pressing against an object. In another aspect, the controller may determine that the surgical instrument is touching an object based on object recognition (e.g., identifying that the area of the object changes based on coming into contact with the instrument).

The controller 20 matches a 3D model of the surgical instrument to (at least a portion of) the first image (at block 34). Specifically, the surgical instrument that is captured within the first image may have a particular position and/or orientation. The controller 20 may retrieve a 3D model 27 of the surgical instrument from memory 28, and may project (e.g., align) the model upon the surgical instrument within the captured image, such that the 3D model matches (e.g., is superimposed above) the surgical instrument (e.g., within a tolerance threshold). In one aspect, the controller may manipulate the 3D model (e.g., adjusting scale, orientation, etc.) within the 3D model space to align (match up) the model with the surgical instrument (e.g., up to or above the tolerance threshold, as described herein). In another aspect, the models 27 may include one or more 3D models of a same surgical instrument, but in different scales and/or orientations. In which case, the controller may be configured to determine the scale and/or orientation of the surgical instrument within the first image, and then retrieve a 3D model that matches the instrument's scale and/or orientation (e.g., up to a tolerance threshold), to select a matching 3D model. For example, the models 27 may include a table of one or more 3D models having different scales and/or orientations, and the controller may perform a table lookup into the data structure to select a stored 3D model with a matching scale and/or orientation.

In one aspect, the controller may retrieve the model based on one or more characteristics of the surgical instrument. For example, the memory 28 may include a table that includes a list of 3D models stored in memory with respect to one or more characteristics, such as unique identifier (e.g., serial number) of the instrument. The controller may determine the one or more characteristics of the surgical instrument and may perform a table lookup into the table to identifier a 3D model associated with the surgical instrument. Once identified, the controller may retrieve the 3D model and may perform a matching operation in order to match the 3D model to the instrument illustrated within the first image.

The controller 20 is configured to estimate a first six dimensional (6D) pose of the surgical instrument at the first location based on the one or more parameters (e.g., determined during calibration of the camera) and the matching 3D model of the surgical instrument in the first image (at block 35). In particular, the 3D model may represent the surgical instrument within a 3D model space. The controller uses the one or more (e.g., intrinsic) parameters of the camera to define the position and orientation of the surgical instrument with respect to a position of the camera. In one aspect, the controller may apply the intrinsic parameters and the 3D model to (e.g., as input into) a 6D pose model, which produces the 6D pose as output. In particular, the 6D pose includes the surgical instruments orientation and location with respect to the camera in (e.g., being at the origin of) a 3D coordinate system, such as a Cartesian coordinate system that includes X, Y, and Z axes. For example, the 6D pose includes the rotation (pitch, yaw, and roll) between the X, Y, and Z axes, and translation along the X, Y, and Z axes from (or with respect to) a reference point, such as the origin (e.g., being the position of the camera) of the 3D coordinate system. In some aspects, the controller may use any known (or future) method (e.g., algorithm) to determine the 6D pose of an object in an image with respect to the camera that captured the image.

The controller receives another (e.g., a second) image from (e.g., video captured by) the camera that includes the surgical instrument 24 at another (e.g., second) location within the field of view of the camera, e.g., touching the object at the second location (at block 36). In particular, the second image may be captured after (e.g., the first image and after) the surgical instrument has been moved (e.g., by the operator) from the first location to the second location in order to estimate positional data associated with both locations. For instance, the positional data may be a distance between the first (starting) location and the second (target or destination) location. In which case, both locations may be disposed on (at least a portion of) an object that is within both received images. In one aspect, the second image may be received in a similar manner as the first image. For instance, the second image may be received responsive to receiving user input (e.g., the operator pressing a button on an input device for the camera to capture the second image). In another aspect, the second image may be received responsive to determining that the surgical instrument is touching the second location of the object. The controller 20 matches the 3D model of the surgical instrument to (e.g., at least a portion of) the second image (at block 37). In one aspect, the controller may use the same 3D model used to match the surgical instrument in the first image to match the surgical instrument in the second image. In this case, the controller may adjust the 3D model (e.g., scale and/or rotate the 3D model) to match the surgical instrument within the tolerance threshold. In another aspect, the controller may be configured to match a different 3D model, with respect to the 3D model used for the first image, to the surgical instrument in the second image.

The controller 20 determines whether the camera has moved (e.g., based on sensor data from the sensor 23) (at decision block 38). In particular, the controller may determine whether the camera has moved from a first position at which the first image was captured by the camera to a second, different position at which the second image was captured by the camera. For example, the sensor may be an IMU, as described herein, which may be coupled to the camera 22, and may produce sensor (e.g., motion) data based on camera movement. The controller may obtain the sensor data and determine whether the camera has moved after capturing the first image and before capturing the second image. In another aspect, the surgical system may include an external (e.g., 6D) tracking system and a marker attached to the camera. In this case, the tracking system may be another camera that is arranged to capture images of the camera 22 that includes the marker, where the controller 20 may be configured to determine whether the camera 22 moves based on detected movement of the marker.

In another aspect, the controller 20 may determine whether the camera 22 has moved based on one or more images (e.g., the first and second images) captured and received from the camera 22. For example, the controller perform a camera motion tracking algorithm (e.g., a Simultaneous Localization and Mapping (SLAM) algorithm, a Visual Odometry (VO) algorithm, etc.) for tracking the movement of a camera based on movement of one or more points within a succession of one or more video frames (images) captured by the camera. In which case, the controller 20 may determine that the second image is captured at a different perspective (e.g., with respect to one or more axes within viewing space of the camera) than a perspective of the first image captured by the camera.

If so, the controller 20 estimates a second 6D pose of the surgical instrument at the second location based on the one or more parameters, the matching 3D model of the surgical instrument in the second image, and/or the detected movement of the camera (at block 39). As described herein, the one or more parameters may be intrinsic parameters of the camera. Upon detecting movement of the camera, the controller may be configured to determine one or more extrinsic parameters of the camera, where the extrinsic parameters indicate changes in the camera's position (e.g., translation) and/or orientation (e.g., rotation) within the environment (e.g., real 3D world). In particular, the controller 20 may apply the intrinsic and extrinsic parameters and the matching 3D model into a 6D pose model (e.g., the model used to determine the first 6D pose) to estimate the second 6D pose of the surgical instrument. Thus, the controller may determine the second 6D pose of the surgical instrument, while considering (e.g., taking into account) the movement of the camera (e.g., which may occur due to the operator manipulating the camera).

As described herein, the camera may be manually manipulated (e.g., moved by an operator adjusting a handle coupled to the camera) in order to move the camera (e.g., in order to capture a different perspective of the surgical site. In which case, the surgical system may determine the movement based on sensor data from the sensor 23. In another aspect, when the camera is coupled to a robotic arm (e.g., arm 4 in FIG. 1), the controller may determine that there was camera movement based on movement of one or more actuators of the arm. For example, the controller may receive one or more control signals generated from spatial state signals (received from one or more UIDs of the system), and may determine how the robotic arm will move based on the generated control signals, which would be used to move the actuators 17 of the arm 4. In another aspect, the surgical system may include one or more (motion) sensors 23 coupled to the arm, and may determine the arm movement based on sensor data.

If, however, the camera 22 has not moved (or the controller has not detected movement based on sensor data), the control estimates the second 6D pose of the surgical instrument at the second location based on the one or more intrinsic parameters of the camera and the matching 3D model of the surgical instrument in the second image (at block 40).

The process 30 continues to FIG. 3b in which the controller determines whether a 3D reconstruction (e.g., a 3D physical representation) of one or more objects within one or more images captured by the camera 22 is available (at decision block 41). In some aspects, the 3D reconstructions may be a 3D physical representation of a surface of an object within one or more captured images. In one aspect, the controller may determine that a 3D reconstruction is available (or may be generated or determined) based on whether the controller may generate such a reconstruction. In particular, the controller may be configured to determine the 3D reconstruction of at least a portion of an object based on one or more images captured by the camera of the system. For example, the controller may generate a reconstruction using the SLAM (and/or VO) algorithm based on (e.g., using) one or more different images (e.g., when the second image is different (e.g., a different perspective from) than the first image). In another aspect, the determination may be based on whether the (e.g., memory 28 of the) surgical system includes a (e.g., predefined) 3D reconstruction of the object.

If a 3D construction is not available, the controller estimates a (e.g., linear) distance between the first and second locations based on the first and second 6D poses of the surgical instrument (at block 42). For example, knowing the 6D poses, the controller may be configured to determine a relative transformation between both poses. For example, the controller may determine a transformation function (e.g., transformation matrix), which when applied to a matrix associated with (e.g., the first location of) the first 6D pose of the surgical instrument in the first image results in a matrix associated with (e.g., the second location of) the second 6D pose of the surgical instrument in the second image. From the relative transformation, the controller may derive the distance between (e.g., two locations of the) two 6D poses. In another aspect, the controller may determine the distance between the two locations using other known (or future) methods.

The controller 20 displays the distance between the first and second locations superimposed above (e.g., overlaid on top of) video of the object (at block 43). For example, the surgical system may display the video of the surgical site captured by the camera 22 as at least some of the operations are being performed to estimate positional data. In which case, once the distance is estimated, the surgical system may display the distance between the two points, such that the surgeon may see the distance, along with a (e.g., straight) line between the two points, which the surgeon may use as a guide line for any surgical tasks (e.g., cutting).

If, however, a 3D reconstruction is available, the controller 20 estimates a distance as a path along the 3D reconstruction of (at least a portion of) the object between the first and second locations based on the first and second 6D poses of the surgical instrument (at block 44). As described herein, the first and second locations of the surgical instruction within the first and second images may be a part of (or on) a portion of an object that is captured by both images. For example, the operator of the surgical system may be trying to measure a distance between two locations on a piece of tissue. In cases, however, when the piece of tissue is not flat (e.g., is instead curved) and/or is textured (e.g., having hills and valleys), the operator may intend for the measurement to be along a path on the surface of the piece of tissue between the two locations. Thus, the controller may be configured to determine the distance using the 3D reconstruction and the relative transformation between the two 6D poses. For instance, once the distance is determined using the relative transformation, the controller may adjust (modify) the distance based on the 3D reconstruction, such that it conforms to a path along the 3D reconstruction.

Some aspects may perform variations to the process 30 described herein. For example, the specific operations of the process may not be performed in the exact order shown and described. The specific operations may not be performed in one continuous series of operations and different specific operations may be performed in different aspects. For example, the operations within dashed boxes may be optional operations that may not be performed while at least a portion of the process 30 is performed. As an example, the process may omit the operations performed in block 31 to calibrate the camera, if the calibration had been previously performed (e.g., during a previous performance of the process 30). In which case, the controller may be configured to retrieve the one or more parameters from memory 28.

As described herein, the controller may determine whether the distance is a path along the 3D reconstruction of the object or a linear distance based on whether a 3D reconstruction of the object is available. In another aspect, the controller may determine which distance to estimate, and display based on user input (e.g., a user selection of a UI item on a GUI displayed on display 25 that indicates which distance the user wishes to view).

Figure 4A:
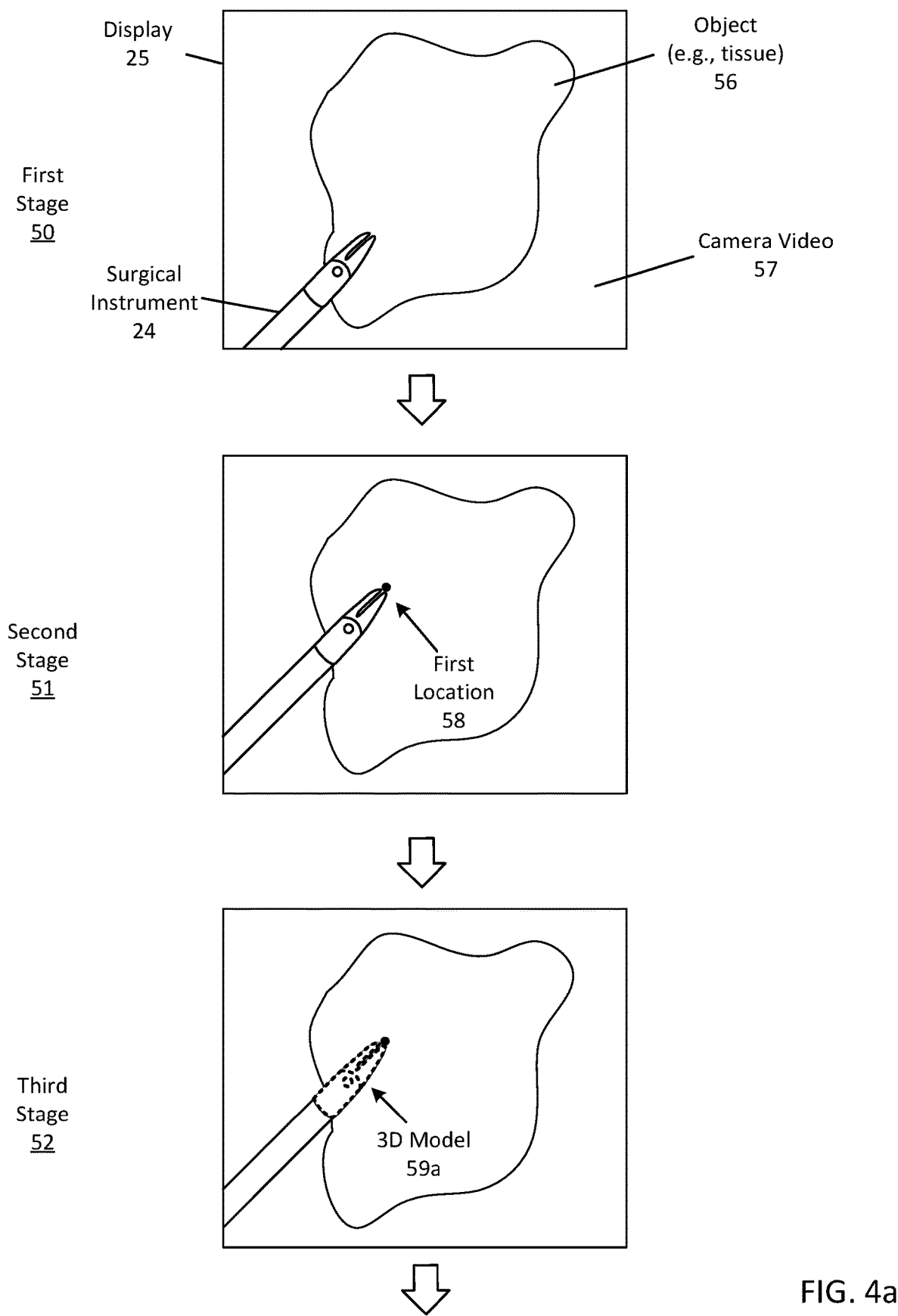
FIGS. 4a and 4b illustrate several stages that show a display with a surgical instrument in which a distance is estimated between two locations at which the surgical instrument touches an object.
Figure 4B:
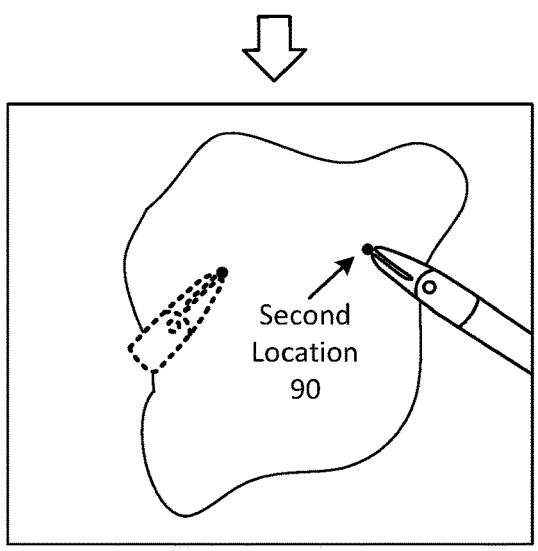
Figure 4B:
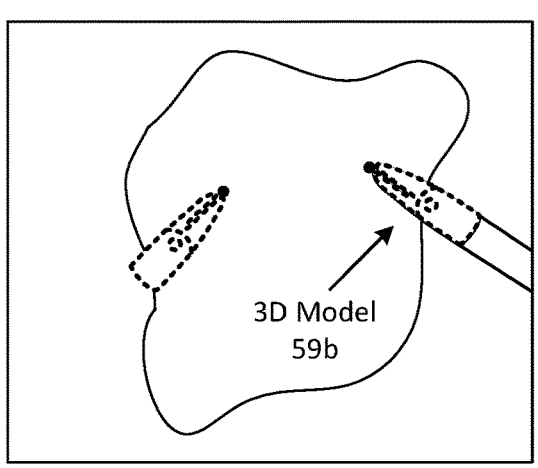
Figure 4B:
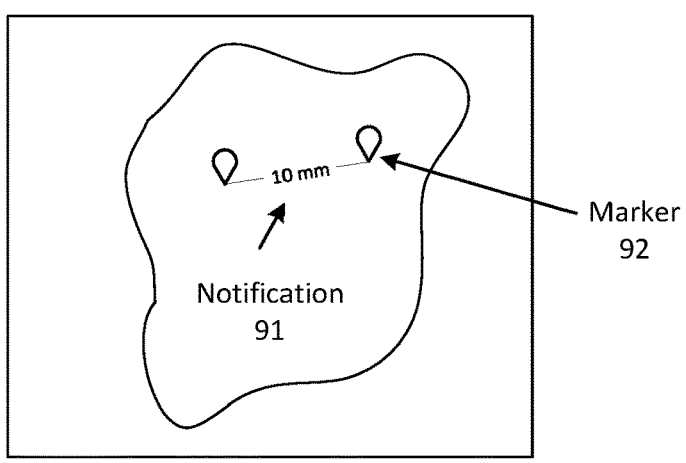

FIGS. 4a and 4b illustrate several stages 50-55 that show video 57 captured by the camera 22 in the display 25 with the surgical instrument 24 in which a distance is estimated between two locations at which the surgical instrument touches an object (e.g., tissue 56) shown in the video 57. In one aspect, these figures illustrate at least some of the operations described in the process 30 of FIGS. 3a and 3b. The first stage 50 shows video 57 captured by the camera 22 displayed on the display 25 that includes the surgical instrument, which is a grasping tool (e.g., having a distal grasping/clamping portion coupled to the surgical instrument), adjacent to the object 56 (e.g., showing the instrument entering the field of view of the camera).

The second stage 51 shows the surgical instrument at a first location 58 on the object. In one aspect, this stage shows the first image received from the camera 22, as described herein in block 33 of process 30 in FIG. 3a. In one aspect, this stage shows the image that may be received in response to receiving user input (e.g., an operator selecting a button that instructs the camera 22 to capture the image. In one aspect, the first location 58 may be a location at which the (e.g., distal end of the) surgical instrument had touched. In another aspect, the location may be a on (or a part of) the surgical instrument. The third stage 52 shows a 3D model 59a aligned (e.g., that matches) and is superimposed above (at least a portion of) the surgical instrument 24. In particular, this stage is showing the result of the controller 20 retrieving a 3D model 59a associated with the surgical instrument, and matching the 3D model to the surgical instrument (e.g., by manipulating the 3D model within the 3D model space).

Turning to FIG. 4b, this figure shows the fourth stage 53 in which the surgical instrument 24 moved to a second location 90. In particular, at this stage the surgeon may have moved the instrument to the second location in order to measure a distance between the first location 58 and the second location 90. In one aspect, this stage shows an image (e.g., the second image, as described herein), which the surgical system may capture responsive to user input, or which may have been captured automatically (e.g., upon detecting that the surgical instrument has touched the second location 90). As described herein, the first location 58 may be a part of the surgical instrument (e.g., a distal end). In which case, the second location 90 may be the same part of the surgical instrument, but at a different location (e.g., about the object 56) within the surgical site (e.g., within the field of view of the camera).

The fifth stage 54 shows a 3D model 59b aligned (e.g., that matches) and is superimposed above the surgical instrument 24. As described herein, the controller may match the 3D model 59b to the surgical instrument. In one aspect, the 3D model 59b may be the same as the 3D model 59a, but having a different position and/or orientation with respect to a position and/or orientation of the 3D model 59a. In which case, the controller may manipulate the model 59a to align with the position and/or orientation of the surgical instrument within the fifth stage 54, as described herein.

The sixth stage 55 shows the result of the controller estimating the distance between the two locations by performing the positional data estimation operations described herein (e.g., using parameters of the camera and aligned 3D models to estimate 6D poses, and from those poses estimating a distance). Specifically, this figure is showing two markers 92, each at one of the first location 58 and the second location 90 and a notification 91 that includes a distance of 10 mm spanning between the two markers. Specifically, the notification includes a line that spans from both markers 92 and text that indicates a distance value, which in this case is 10 mm, and which may correspond to the length of the line. In one aspect, the notification (and/or the markers) are UI items that are overlaid on top of (e.g., superimposed above) the (e.g., second image used match the 3D model with the surgical instrument at the second location shown in the) video 57. In one aspect, the UI items may be continuously displayed at the portion of the object that is being measured, so long as the portion of the object is within the field of view of the camera 22. As shown herein, the distance is a linear distance between the two markers. In another aspect, the distance may be a curved path along a surface of the object 56, when a 3D reconstruction is available for the object, as described herein.

Figure 5:
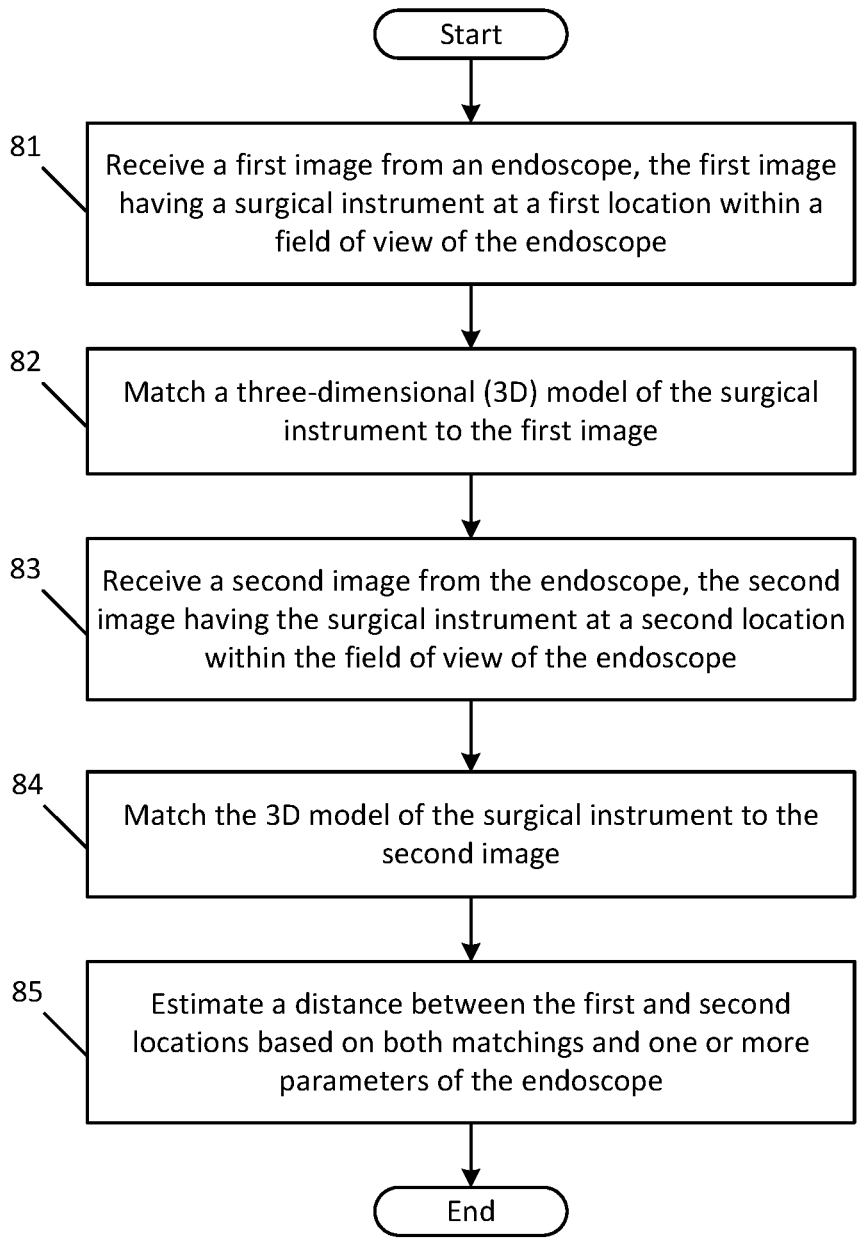
FIG. 5 is a flowchart of a process for another aspect of estimating a distance between two locations using images received from an endoscope of the surgical system.

FIG. 5 is a flowchart of a process 80 for another aspect of estimating a distance between two locations using images received from an endoscope 22 of the surgical system 1. The controller 20 receives a first image from an endoscope 22, the first image having a surgical instrument 24 at a first location within a field of view of the endoscope (at block 81). The controller matches a 3D model of the surgical instrument to the first image (at block 82). In particular, the controller matches (aligns) the 3D model of the instrument to the instrument that is shown within the first image. The controller 20 receives a second image from the endoscope, the second image having the surgical instrument at a second location within the field of view of the endoscope (at block 83). The controller matches the 3D model of the surgical instrument to the second image (at block 84). The controller estimates a distance between the first and second locations based on both matchings and one or more (e.g., intrinsic) parameters of the endoscope (at block 85).

Figure 6:
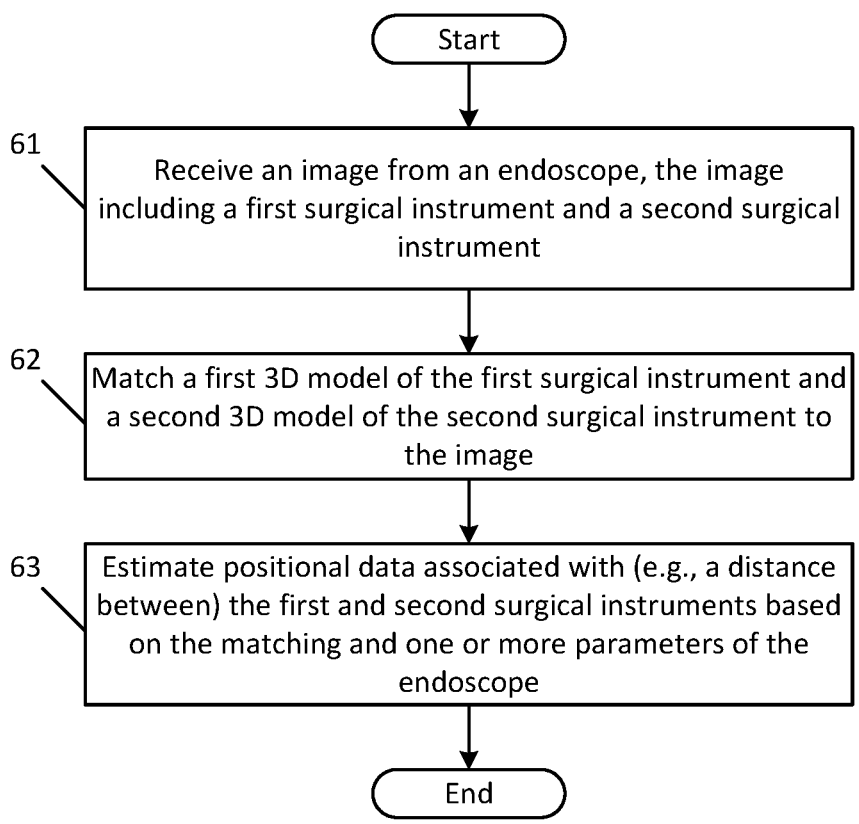
FIG. 6 is a flowchart of a process for an aspect of estimating a distance between two surgical instruments using images received from an endoscope of a surgical system.

As described thus far, the surgical system 1 may be configured to estimate positional data based on captured images that includes a surgical instrument, such as a distance between two different locations of the surgical instrument. In another embodiment, positional data may be estimated using images that include two or more surgical instruments. FIG. 6 is a flowchart of a process 60 for an aspect of estimating a distance between two surgical instruments using images received from an endoscope 22 of a surgical system 1. The controller 20 receives an image from (e.g., captured by) an endoscope, the image including a first surgical instrument and a second surgical instrument (at block 61). For example, the first surgical instrument may be a grasping tool (e.g., similar to the instrument shown in FIGS. 4a and 4b, and the second surgical instrument may be a scalpel. In one aspect, each of the surgical instruments may be arranged to be individually manipulated (e.g., when manually manipulated via individual handles) by a user of the surgical system. In another aspect, at least one of the surgical instruments may be coupled to (e.g., a distal end of) a robotic arm of the surgical system.

The controller 20 matches a first 3D model of the first surgical instrument and a second 3D model of the second surgical instrument to the image (at block 62). In particular, the controller may retrieve a first 3D model (from models 27 in memory 28) that is associated with the first surgical instrument, and retrieve a second 3D model that is associated with the second surgical instrument, and may align both 3D models to their respective surgical instruments, as described herein.

The controller 20 estimates positional data associated with (e.g., a distance between) the first and second surgical instruments based on the matching and one or more parameters of the endoscope (at block 63). For example, the controller may estimate a distance between (e.g., two points associated with) the two surgical instruments by estimating their respective 6D poses, and then using the relative transformation between the 6D poses to determine the distance, as described herein. In one aspect, the distance may be estimated between a particular point (e.g., a distal end) on each of the surgical instruments. In another aspect, the distance along an object may be estimated between locations at which one or both of the surgical instruments have touched the object.

Thus, unlike the estimation of the distance described in FIGS. 3a and 3b, the distance between the two surgical instruments may be estimated using one image. In another aspect, the controller may perform one or more operations described in those figures, when estimating the positional data with two (or more) surgical instruments. For example, the controller may determine whether a 3D reconstruction of an object within the received image is available (e.g., based on whether one or more images have been received), and if so, the estimated distance between the two surgical instruments may be along the 3D reconstruction, as described herein. For example, the controller may receive an image that includes an object that is at least partially behind two surgical instruments (e.g., where a surgeon may be touching different locations of the object with each of the instruments). The controller may determine a 3D physical representation of a surface of the object (at least along a portion between the two instruments), and determine positional data that includes an estimated surface distance along the 3D representation of the surface between the two instruments. In one aspect, the estimated surface distance may be a shortest distance between points of both instruments with respect to physical characteristics of the surface.

Figure 7:
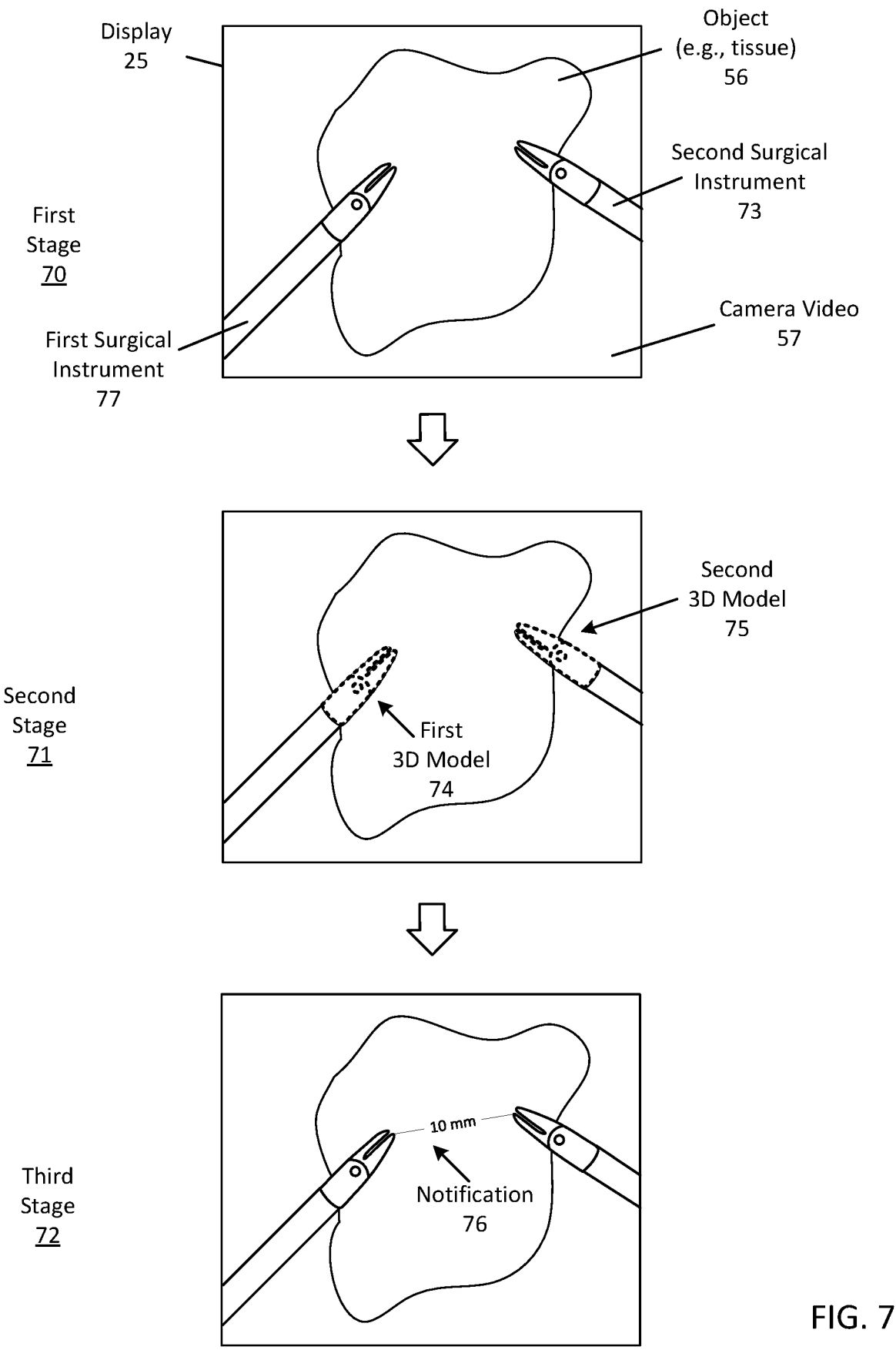
FIG. 7 illustrates several stages that show a display with two surgical instruments in which a distance is estimated between the two instruments.

FIG. 7 illustrate several stages 70-72 that show video 57 in the display 25, which includes with two surgical instruments 77 and 73 and an object (e.g., tissue) 56 (e.g., within a field of view of the camera), in which the surgical system estimates a distance between the two instruments. The first stage 70 shows the video 57 captured by the camera 22 that is being displayed within the display that includes a first surgical instrument 77 and a second surgical instrument 73, both of which are grasping tools. In one aspect, this stage is showing how the surgeon has positioned the instruments about the object in order for the system to estimate and display a distance between the instruments.

In one aspect, the controller may receive the image of the two surgical instruments at this stage. For example, once the surgeon has placed both the instruments at their respective locations in order to estimate a distance between the instruments, the surgeon may provide user input (e.g., selecting a button, as described herein), for the controller to receive the image (and to estimate the distance between the instruments). In another aspect, the controller may automatically receive the image for estimating the distance, as described herein.

The second stage 71 shows a first 3D model 74 of the first surgical instrument 77 matching the first instrument and a second 3D model 75 of the second surgical instrument 75 matching the first instrument (e.g., in the image of the first stage 70 received by the controller 20). As described herein, the controller may be configured to manipulate both 3D models such that they are aligned (within a tolerance threshold) with their respective instruments. In one aspect, although shown as overlapping (at least a portion of) their respective instruments, this may be for only illustrative purposes. In which case, the video 57 displayed in the second stage 71 may be the same (or similar) as the video shown in the first stage 70.

The third stage 72 shows the result of the controller estimating the distance between the two surgical instruments by showing a notification 76 that includes a line that extends from a first (e.g., distal) end or location of the first instrument 77 to a second (e.g., distal) end or location of the second instrument 73 that includes the distance (e.g., 10 mm) between the two locations. As described herein, the controller may estimate the distance by estimating 6D poses of each respective instrument, and then estimating a relative transformation between both 6D poses (e.g., a transformation which when applied to one of the 6D poses results in the other 6D pose).

As described herein, the distance 76 may be estimated between the two instruments. In one aspect, the controller may continuously update the distance based on changes to one or both of the instruments. For example, as the surgeon moves the second surgical instrument 73 away from the first surgical instrument 77, the controller may recalculate the second instrument's 6D pose based on changes to the instrument's aligned 3D model (and/or recalculate the first instrument's 6D pose), and from this estimate and display a new distance between the two instruments. As a result, the notification 76 may update as the surgeon moves at least one of the instruments to provide the surgeon with real-time positional data updates.

As described thus far, at least some of the operations performed by the surgical system may be performed intraoperatively. For example, the surgical instrument may estimate positional data, such as a distance between two surgical instruments in real-time in order to provide a surgeon with real-time up-to-date measurements during a surgical procedure. In another aspect, at least some of the operations may be performed postoperatively. In which case, the controller 20 may be configured to receive a video stream (or one or more video streams), which were previously captured (and stored in memory 28) by the camera 22, and may be configured to estimate positional data using the video stream. In which case, the controller may receive user input, from which the controller may estimate the positional data. As an example, referring to FIG. 7, when these operations are performed postoperatively, the controller may be configured to receive a user instruction to receive an image of the video stream from which the user is interested in positional data. For example, as the user is viewing the video stream, the scene shown in the first stage 70 may be presented. Once shown, the user may wish to see the distance between the surgical instruments. In response, the user may select a button, which may provide the controller with a control signal, instructing the controller to estimate a distance between the instruments, as described herein. As a result, the positional data estimation operations performed by the controller may allow a user to view the data after a surgical procedure is performed.

As described thus far, an example of positional data of one or more surgical instruments that may be estimated is a distance (e.g., between surgical instruments). Other types of positional data are possible. For example, the estimation of the 6D pose of a surgical instrument may be performed one or more times (e.g., along a length of a surgical procedure). In which case, the surgical system may estimate (and display) a travel path (e.g., along a surgical site) of a surgical instrument, with respect to the camera 22. As another example, the positional data may include one or more position statistics of a surgical instrument, such as how long a surgical instrument had remained at a particular (or within a threshold distance of) position, how often the surgical instrument moved, and an average orientation of the surgical instrument (e.g., which may be based on the instruments average 6D pose through a surgical procedure). In one aspect, this estimated positional data may be displayed (e.g., overlaid on top of) the video 57, as described herein, and/or may be provided within a report produced by the surgical system.

As described herein, the surgical system estimates a distance between at least two locations using one or more 3D models. In one aspect, each location may correspond to a point (or portion) of an object captured within one or more images by a camera of the surgical system. In another aspect, a location may be a point of an object that a portion (e.g., a distal end) of a surgical instrument that is captured within an image is in contact with. In another aspect, the location may be a spot on the object at which at least one surgical instrument has touched. In another aspect, the location may be a point (or portion) of the surgical instrument, such as the instrument's distal end, which is within one or more images captured by the system. In which case, the location relative to the surgical instrument may be predefined.

While certain aspects have been described and shown in the accompanying drawings, it is to be understood that such aspects are merely illustrative of and not restrictive on the broad invention, and the invention is not limited to the specific constructions and arrangements shown and described, since various other modifications may occur to those of ordinary skill in the art. The description is thus to be regarded as illustrative instead of limiting.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

As previously explained, an aspect of the disclosure may be a non-transitory machine-readable medium (such as microelectronic memory) having stored thereon instructions, which program one or more data processing components (generically referred to here as a "processor") to automatically (e.g., without user intervention) estimate positional data (e.g., distances between two locations) using one or more images, as described herein. In other aspects, some of these operations might be performed by specific hardware components that contain hardwired logic. Those operations might alternatively be performed by any combination of programmed data processing components and fixed hardwired circuit components.

While certain aspects have been described and shown in the accompanying drawings, it is to be understood that such aspects are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A surgical system comprising:
    a surgical instrument;
    a display;
    an endoscope configured to capture images of a surgical site within a field of view of the endoscope;
    at least one processor; and
    memory having stored therein instructions which when executed by the at least one processor causes the surgical system to:
        receive a first image from the endoscope that includes the surgical instrument at a first location within the surgical site,
        match a three-dimensional (3D) model of the surgical instrument to the first image,
        receive a second image from the endoscope that includes the surgical instrument at a second location, which is different than the first location, within the surgical site,
        match the 3D model of the surgical instrument to the second image,
        estimate a distance between both locations that is determined from both matchings and one or more parameters associated with the endoscope, and
        display the distance between both locations superimposed over the surgical site on the display.

2. The surgical system of claim 1, wherein the one or more parameters of the endoscope comprises at least one of a focal length of a lens of the endoscope, a principal point associated with the lens, and a distortion of the lens.

3. The surgical system of claim 1, wherein the memory has further instructions to:
   estimate a first pose of the surgical instrument at the first location based on the one or more parameters of the endoscope and the matching 3D model of the surgical instrument in the first image; and
   estimate a second pose of the surgical instrument at the second location based on the one or more parameters of the endoscope and the matching 3D model of the surgical instrument in the second image,
   wherein the distance is estimated using the first and second poses.

4. The surgical system of claim 3, wherein the second image is received after the first image, wherein the memory has further instructions to determine that the endoscope has moved from a first position at which the first image was captured by the endoscope to a second, different position at which the second image was captured by the endoscope, wherein the second pose is determined based on the movement of the endoscope.

5. The surgical system of claim 3, wherein the first and second locations are on a portion of an object that is within the first and second images, wherein the second image is of a different perspective of the object than the first image, wherein the memory has further instructions to determine a 3D reconstruction of the portion of the object based on the first and second images, wherein the estimated distance is of a path along the 3D reconstruction of the portion of the object between the first and second locations.

6. The surgical system of claim 1, wherein the surgical instrument is arranged to be manually manipulated by a user.

7. The surgical system of claim 3, wherein the memory has further instructions to display 1) a first marker at the first location and a second marker at the second location and 2) the estimated distance overlaid on top of the second image.

* * * * *